United States Patent [19]
Hoke et al.

[11] Patent Number: 5,596,090
[45] Date of Patent: Jan. 21, 1997

[54] ANTISENSE OLIGONUCLEOTIDES DIRECTED AGAINST HUMAN VCAM-1 RNA

[75] Inventors: Glenn D. Hoke, Mt. Airy; Matthews O. Bradley, Laytonsville, both of Md.; Taffy J. Williams, Lansdale, Pa.; Che-Hung Lee, Silver Spring, Md.

[73] Assignee: The United States of America as represented by the Secretary of the Navy, Washington, D.C.

[21] Appl. No.: 137,701

[22] Filed: Oct. 12, 1993

Related U.S. Application Data

[63] Continuation-in-part of Ser. No. 918,256, Jul. 24, 1992, abandoned.

[51] Int. Cl.$^6$ .......................... C07H 21/04; A61K 31/70
[52] U.S. Cl. ...................... 536/24.5; 536/23.1; 536/24.1; 536/24.3; 536/24.31; 435/6
[58] Field of Search .................... 435/6, 91.1, 172.3, 435/172.1; 536/23.1, 24.1, 24.5, 24.3, 24.31; 514/44

[56] References Cited

U.S. PATENT DOCUMENTS 5,272,263  12/1993  Hession et al. .................. 536/23.5

FOREIGN PATENT DOCUMENTS 9203139  3/1992  WIPO.

OTHER PUBLICATIONS

Stein et al. Science 261:1004 (1993).
Milligan et al. J. Med. Chem. 36:1924 (1993).
Uhlmann et al. Chemical Reviews 90:544 (1990).
Chiang et al. J. Biol. Chem. 266:18162 (1991).
Leamon et al. PNAS 88:5572 (1991).

*Primary Examiner*—John L. Leguyader
*Attorney, Agent, or Firm*—A. D. Spevack, Esq.; William Garvert, Esq.

[57] ABSTRACT

Antisense oligonucleotides complementary to human mRNAs or pre-mRNAs coding for VCAM-I are used in a therapeutic treatment of sepsis (sepsis, the sepsis syndrome, septic shock and all other manifestations of the sepsis disease, including but not inclusive of, adult respiratory distress syndrome, multi-organ failure, or cardiovascular dysfunction).

3 Claims, 2 Drawing Sheets

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES     ( x i ) SEQUENCE DESCRIPTION: SEQ ID NO:1:

GCCTGGGAGG GTATTCAGCT C        21

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES     ( x i ) SEQUENCE DESCRIPTION: SEQ ID NO:2:

AACCCTTATT TGTGTCCCAC C        21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES     ( x i ) SEQUENCE DESCRIPTION: SEQ ID NO:3:

CCCAGGCATT TTAAGTTGCT G        21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES ( x i ) SEQUENCE DESCRIPTION: SEQ ID NO:4:

CACGAGGCCA CCACTCATCT C                                                                 21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES     ( x i ) SEQUENCE DESCRIPTION: SEQ ID NO:5:

CTTTGACTTC TTGCTCACAG C                                                                 21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES     ( x i ) SEQUENCE DESCRIPTION: SEQ ID NO:6:

AACTCCTCCA GTTCTCTCAT C                                                                 21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES     ( x i ) SEQUENCE DESCRIPTION: SEQ ID NO:7:

TTTAAGCAAT CTTGCTATGG C                                                                 21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: YES     ( x i ) SEQUENCE DESCRIPTION: SEQ ID NO:8:

TCCTGAAGCC AGTGAGGCCC G                                                                 21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (iii) HYPOTHETICAL: NO (iv) ANTI-SENSE: YES (xi) SEQUENCE DESCRIPTION: SEQ ID NO:9:

ACCTGTGTGT GCCTGGGAGG G 21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (iii) HYPOTHETICAL: NO     (iv) ANTI-SENSE: YES     (xi) SEQUENCE DESCRIPTION: SEQ ID NO:10:

CGTGATGAGA AAATAGTGGT T 21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (iii) HYPOTHETICAL: NO     (iv) ANTI-SENSE: YES     (xi) SEQUENCE DESCRIPTION: SEQ ID NO:11:

CGACCATCTT CCCAGGCATT T 21

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear     (iii) HYPOTHETICAL: NO     (iv) ANTI-SENSE: YES     (xi) SEQUENCE DESCRIPTION: SEQ ID NO:12:

CCACCACTCA TCTCG 15

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (iii) HYPOTHETICAL: NO     (iv) ANTI-SENSE: YES     (xi) SEQUENCE DESCRIPTION: SEQ ID NO:13:

CCCATTCACG AGGCCACC 18

(2) INFORMATION FOR SEQ ID NO:14:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: YES ( x i ) SEQUENCE DESCRIPTION: SEQ ID NO:14:

CGAGGCCACC ACTC                                                                      14

( 2 ) INFORMATION FOR SEQ ID NO:15:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:15:

CCTCCAGTTC TCTC                                                                      14

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:16:

CTCTCATCTT GATGGC                                                                    16

( 2 ) INFORMATION FOR SEQ ID NO:17:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:17:

GCCAGTGAGG CCCG                                                                      14

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( x i ) SEQUENCE DESCRIPTION: SEQ ID NO:18:

CCTGGGAGGG TATTC                                                                    15

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:19:

CCCTTATTTG TGTCCC                                                                   16

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:20:

GGTTCCAAAA CCCTT                                                                    15

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:21:

TTTGTGTCCC ACCTG                                                                    15

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:22:

CATCTTCCCA GGCAT                                                                    15

ANTISENSE OLIGONUCLEOTIDES DIRECTED AGAINST HUMAN VCAM-1 RNA

RELATED APPLICATION

This application is a Continuation-in-Part of application 07/918,256, filed 24 Jul. 1992, now abandoned.

BACKGROUND OF THE INVENTION

1. Field of the Invention

This invention relates to agents and therapy to lessen morbidity and mortality by protecting against septic shock, Adult Respiratory Distress Syndrome (ARDS), and other inflammatory complications of shock. Particularly, this invention relates to the treatment of septic shock and the other complications resulting from septic shock by down-regulating the expression of certain cell-cell adhesion receptors or ligands involved in the inflammatory response during septic shock. More specifically, this invention relates to therapy with antisense oligonucleotides which reduce expression of adhesive proteins and protect against septic shock and reduce associated inflammatory damage (like ARDS). Particularly this invention relates to the use of antisense oligonucleotides complementary to human mRNAs or pre-mRNAs coding for VCAM-I to be used in a therapeutic treatment of sepsis (henceforth to include sepsis, the sepsis syndrome, septic shock and all other manifestations of the sepsis disease, including but not inclusive of, adult respiratory distress syndrome, multi-organ failure, or cardiovascular dysfunction). Mediators of sepsis produce endothelial dysfunctions that result in the development of an intravascular inflammatory response and subsequent damage to the endothelial cells with migration of leukocytes into the surrounding tissues. This invention also relates to the treatment of sepsis with antisense oligonucleotides targeted to cellular based receptors or their ligands where these receptors or ligands are involved in the inflammatory response during the development of sepsis. This invention further relates to the inhibition of the synthesis of VCAM-I with antisense oligonucleotides.

2. Description of the Prior Art

Septic shock is defined as a type of shock associated with overwhelming infection. Most commonly, the infection is produced by gram-negative bacteria although other bacteria, viruses, fungi and protozoa may also be causes. As summarized in Infectious Diseases and Medical Microbiology, 2nd edition, edited by Braude et al., Chapter 92, pages 700 et seq.

"Shock is a syndrome of generalized metabolic failure resulting from prolonged inadequacy of tissue perfusion. Its early clinical manifestations reflect malfunction of those organs most dependent on uninterrupted blood flow, particularly the brain, as well as compensatory adjustments designed to maintain adequate arterial pressure. As these adjustments fail, urinary output decreases and biochemical indices of distorted metabolism are detectable; specifically nonoxidative glycolysis with low yield of high energy chemical bonds testifies to the widespread nature of the disorder. In the end, it is the failure of energy production rather than damage to a particular organ that leads to death.

Other terms, such as 'circulatory collapse,' 'circulatory failure,' and 'hypoperfusion,' have been substituted for 'shock' in an attempt to pinpoint the specific nature of the derangement. When it occurs as a specific complication of infection, it is referred to as 'infectious shock,' 'septic shock,' 'bacteremic shock,' and even 'endotoxin shock.' The last three terms specifically implicate bacterial infection and are therefore too restrictive. Because 'infectious shock' is sufficiently broad as well as concise, this term will be used in the present chapter.

Shock may occur in the course of almost any severe infection, but it is particularly characteristic of bacteremia due to gram-negative bacilli. The importance of endotoxin, the lipopolysaccharide (LPS) composing part of all gram-negative cell walls, is readily apparent because it produces a similar syndrome in experimental animals. Partly because of the extensive use of endotoxin as an investigative tool, endotoxin shock is commonly regarded as the prototype of infectious shock." The shock is believed to be caused by the action of endotoxins, other products of the infectious agent, or host mediators released in response to the infectious agent on the vascular system. Such action causes altered patterns of perfusion of tissues and large volumes of blood to be sequestered in the capillaries and veins.

Sepsis, the sepsis syndrome, and septic shock are not discrete entities, but rather terms that delineate increasingly severe stages of the same disease. Septic shock, a frequently fatal reaction following bacterial infection, has been estimated to occur at a rate of 175 per 100,000 people yearly in the general population and rises to 500 per 100,000 for those people admitted to hospitals (Johnston, J. (1991) J. NIH 3: 61–65). Estimates range up to 400,000 cases of sepsis, 200,000 bouts of septic shock, and 100,000 deaths annually in the United States due to the septic shock induced syndrome (Snell, J. and J. E. Parrillo (1991) Chest 99: 1000–1009). Up to 40–50% of patients who develop septic shock die. The manifestation of septic shock involves a severe decrease in systemic vascular resistance and maldistribution of blood flow. Septicemia, a systemic disease associated with the presence and persistence of pathogenic microorganisms or their toxins in the blood, is currently ranked as the thirteenth leading cause of death in the United States (Annual Summary of Births, Marriages, Divorces, and Deaths: United States, 1988. Hyattsville, Md.: U.S. Department Health and Human Services, Public Health Service, CDC, 1989: 7. Monthly vital statistics report. 1989: 37[13]). Reasons underlying this high incidence of death from septic shock involve increased usage of cytotoxic and immunosuppressive drug therapies which impairs host defense mechanisms or increased use of invasive diagnostic devices or increased patient age (Snell, J. and J. E. Parrillo (1991) Chest 99: 1000–1009). Further causes of impaired host defense mechanisms include diabetes, malignant neoplasms, cirrhosis or extensive burns. The rising rate of infections from organisms other than gram-negative bacteria also contribute to the rise in septic shock induced death. Any bacteria can cause septic shock, however, the gram-negative bacteria (E. coli, Pseudomonas sp. and Bacteroides sp.) in particular evoke septic shock due to the presence of lipopolysaccharide (LPS) in their cell walls. Bacterial LPS, also known as endotoxin, at concentrations as low as a few µg/L can activate immune cells. The majority of damage induced from the presence of LPS is not due to the actual LPS itself, but is in fact a result of the body's complex reaction to the foreign LPS. This response is mediated by immune cell activation and the resultant damage that these activated cells cause to the host tissues.

Septicemia is difficult to reverse and the preferred treatment following the initial signs of hypoperfusion or shock include infusion of normal saline or lactated Ringer's solution. If shock persists then an aggressive fluid challenge is begun and the use of dopamine and/or norepinephrine is recommended. Cardiovascular insufficiency results from alterations to the myocardium and the vasculature and it is myocardial dysfunction that is responsible for hypotension or multiple organ system failure (Snell, J. and J. E. Parrillo (1991). Chest 99: 1000–1009). Unresponsive hypotension usually results from low systemic vascular resistance due to cardiovascular insufficiency which can not be corrected by any therapy. Multiple organ failure usually affects the lungs, kidneys, liver, heart, and central nervous system.

Treatment of septic shock is complex, requiring therapies directed at ameliorating the source of infection [antibiotics], blocking effects of products of the infectious agent and inflammatory mediators on tissues [anti-endotoxin (patent Young et al. U.S. Pat. No. 4,918,163) and anti-cytokine agents (patent Mandell et al. U.S. Pat. No. 4,965,271)], and maintenance of cardiovascular function [volume expansion and pressor agents]. However, mortality still runs at about 100,000 patients per year (40 to 50% of those in shock) and no therapies are available to prevent vascular contractile defects.

Other current approaches to the treatment of sepsis or septic shock involve neutralization of LPS with specific monoclonal antibodies, interference of cytokine-mediated immune responses, or inactivation of cell adhesion proteins with monoclonal antibodies. Targeting of LPS mediated sepsis, however, will be effective only against gram-negative bacteria since LPS is only found in their cell walls. Monoclonal antibodies to the lipid A domain of LPS have had some success at intervention with LPS mediated septic shock from gram-negative bacteria, but not for non-gram-negative induced septic shock (Ziegler, E. J. et al. (1991) N. Eng. J. Med. 324: 429–436). Thus, while the gram-negative LPS may be the most potent inducer of sepsis, gram-positive bacterial infections occur in 60–70% of all cases. Intervention with cytokine mediated activation of the immune response as a means of preventing septic shock would not only interfere with gram-negative induced sepsis, but also shock caused by gram-positive bacterial infection or other agents. The development of an effective therapy to treat all bacterial induced septic shock would be of obvious benefit to patients who are at an increased risk of bacterial induced sepsis and provide increased survival from septic shock and the complications that arise during septic shock induced dysfunctions. Another approach would be interference with the cellular response to the various endogenous mediators (cytokines, PAF, arachidonic acid metabolites, histamine, endorphins, etc) responsible for vasculature effects. These approaches are not currently approved for therapy and are in clinical trials.

One of the major effects experienced by the vasculature is destruction of endothelial cells by leukocytes. Inflammation is characterized by the local accumulation of leukocytes, plasma proteins, and fluid usually at an extravascular site. Inflammatory processes are intrinsically destructive to the surrounding tissues and may, in certain circumstances such as allograft rejection or sepsis, be more harmful than beneficial. Thus, an appropriate strategy for the treatment or prevention of sepsis or septic shock would be down-regulation, but not total ablation, of the inflammatory response. Down-regulation of specific cell adhesion receptors and/or ligands to the receptors would be one approach to preventing, or lessening, the inflammatory mediated damage to endothelial cells in the vasculature.

The involvement of the immune response in the development of septic shock and its lethal consequences provides a target that is applicable to the use of antisense oligonucleotides. Antisense oligonucleotides can be used to inhibit expression of the key receptors and cellular ligands involved in the activation of the immune response. The migration of leukocytes into tissues is the central event in the immune or inflammation response. This migration to and subsequent emigration into the tissue is responsible for the successful host response to injury and infection. The leukocytes are also potentially harmful and contribute to the pathology of many inflammatory disorders. The precise mechanism of this injury is not known, but the generation of free oxygen radicals and release of proteolytic enzymes have been implicated and may act together in leukocyte induced endothelial cell damage (Varani, J. et al. (1989), Am. J. Path. 135: 429–436). Evidence for the leukocyte adhesion to endothelial cells has been attributed to specific surface proteins.

There are many lines of evidence that indicate that inflammatory reactions are modulated by the interaction of circulating leukocytes with adhesion molecules on the endothelial cells of the luminal surface of blood vessels. These vascular adhesion molecules arrest circulating leukocytes and, thus, perform the first step in recruitment of these cells to sites of inflammation. Two cytokine inducible adhesion molecules, ICAM-1 and ELAM-1, found on the surface of the leukocytes have been characterized as important to the recruitment of circulating leukocytes to the sites of inflammation (Simmons, D. et al. (1988) Nature 331: 624–627; Staunton, D. E. et al. (1988) Cell 52: 925–933; Staunton, D. E. et al. (1989) Nature 339: 61–64). However, neither ICAM-1 or ELAM-1 appear to be involved in the recruitment or adhesion of lymphocytes, B- or T-cells, to activated endothelial cells. ELAM-1 is selective for PMNs, and perhaps monocytes, but does not bind lymphocytes (Bevilacqua, M. P. (1987) Proc. Natl. Acad. Sci. USA 84: 9238–9242; Bevilacqua, M. P. (1989) Science 243: 1160–1165). ICAM-1 is the ligand for the leukocyte integrin receptor molecule, LFA-1, however, antibodies against LFA-1 do not block the adhesion of lymphocytic cells to activated endothelial cells (Haskard, D. et al. (1986) J. Immunol. 137: 2901–2906). The above results suggest another pathway for lymphocyte adhesion to activated endothelium.

A prominent feature of endothelial cell activation by cytokines or endotoxin is the alteration of their surface adhesive properties due to the induction of adhesion molecules expression (Pober, J. S. and R. S. Cotran (1990) Physiol. Rev. 70: 427–451). The induction of these molecules leads to the hyperadhesive surface changes observed in vivo during various physiological conditions. Vascular cell adhesion molecule 1 (VCAM-1) was identified in activated human umbilical endothelial cells by expression cloning (Osborne, L. et al. (1989) Cell 59: 1203–1211) and specific monoclonal antibodies (Rice, G. E. and M. P. Bevilacqua (1989) Science 246: 1303–1306). VCAM-1 is an inducible endothelial cell surface molecule which has been demonstrated to mediate intercellular adhesion via interaction with the integrin VLA-4, which is expressed on monocytes, lymphocytes, basophils, eosinophils, and certain tumor cells, but not neutrophils (Elices, M. J. et al. (1990) Cell 60: 577–584; Taichman, D. B. et al. (1991) Cell Regul. 2: 347–356; Bochner, B. S. et al. (1991) J. Exp. Med. 173: 1553–1556; Rice, G. E. et al. (1990) J. Exp. Med. 171: 1369–1374). VCAM-1 expression is inducible on vascular endothelium in pathological conditions, however, it is constitutively expressed on some nonvascular cells (Rice, G. E. et al. (1990) J. Exp. Med. 171: 1369–1374; Rice, G. E. et al. (1991) AM. J. Pathol. 138: 385–393). In the inflammatory process, VCAM-1 is upregulated at the level of translation on endothelial cells of the postcapillary venules (Briscoe, D. M. et al. (1991) Transplantation 51: 537–547).

VCAM-1 is a transmembrane protein and a member of the immunoglobin gene superfamily. Contained within the VCAM-1 molecule are six immunoglobin-like domains which interact with the VLA-4 receptor on lymphocytes. Several lines of evidence are consistent with an important role for VCAM-1 in lymphocyte recruitment in the inflammatory process: 1) VCAM-1 expression is rapidly induced by the cytokines interleukin-1 and tumor necrosis factor alpha and this induction is sustained for up to 72 hours. This time course of VCAM-1 induction parallels the sustained mononuclear lymphocytic infiltration that occurs in delayed hypertension reactions (Dvorak, H. F. et al. (1980) Int. Rev. Exp. Pathol. 21: 195–199). 2) Human umbilical vein endothelial cells (HUVEC) express ICAM-1 and ELAM-1 upon exposure to cytokines and their expression occurs at sites of cytokine injection in vivo (Cotran, R. S. and Pobar, J. S. (1988) In Endothelial Cell Biology, N. Simionescu and M. Simionescu, eds.(New York: Plenum Press), pp. 335–347). HUVEC also express VCAM-1 upon exposure to cytokines (Osborne, L. et al. (1989) Cell 59: 1203–1211). 3) Frozen sections of human synovium exhibit the capacity for binding of lymphocytes to inflamed vessels and not normal vessels, consistent with the presence of inducible VCAM-1 at these sites. Taken together, these results suggests that VCAM-1 may be the central mediator of lymphocyte recruitment to the sites of inflammation in vivo. While the role of VCAM-1 in the adherence of resting T-cells to interleukin-1 stimulated endothelial cells has been suggested, there is little evidence that VCAM-1 is involved in the binding of either activated T-cells or in the transendothelial migration of T-cells (Oppenheimer-Marks, N. et al. (1991) J. Immunol. 147: 2913–2921). Also, VCAM-1 does not appear to play a vital role in the adherence of activated T-cells to endothelial cells.

Based upon the above information, it may be possible to inhibit the binding of resting T-cells to either unstimulated or activated endothelium by disruption of the recognition that occurs between VCAM-1 and VLA-4. The use of monoclonal antibodies against either VLA-4 and/or VCAM-1 can be useful in preventing the recognition of the receptor/ligand pair for each other. Another possible approach for interfering with the recognition process is via a down-regulation of VCAM-1 synthesis and, thereby, a reduction in the presentation of this molecule to the surface of activated endothelial cells. Antisense oligonucleotides provide an attractive approach for inhibiting the presentation of VCAM-1 molecules to the surface of endothelial cells.

Involved in the activation of the inflammatory and immune response, as during the development of sepsis and septic shock, is the expression of many essential cell adhesion proteins and receptors. Adhesion molecules are activated by various cellular mediators, exogenous or endogenous to the host, and therefore, the logical approach is down-regulation of adhesion protein expression as opposed to treatments aimed at the multiple activators. Thus, the use of antisense oligonucleotides to specifically down-regulate adhesion protein expression would be of obvious advantage to most therapeutic approaches to septic shock.

Research by others into PKC inhibition and treatment of inflammatory responses have disclosed that endothelial cells express adhesive proteins in response to sepsis associated stimuli such as endotoxin or cytokines, such as interleukin-1 (IL-1) and Tumor Necrosis Factor (TNF). Magnuson, D. K. et al. ((1989) Surgery 106: 216–223) and Lane, T. A. et al. ((1990) Biophys. Res. Comm. 172: 1273–1281) have shown that these adhesive proteins can be reduced on endothelial cell surfaces by inhibition of PKC with staurosporine or 1-(5-isoquinolinylsulfonyl)-2-methyl piperazine (H7). Surface presentation of these adhesive proteins enhances white blood cell infiltration and activation which can result in tissue damage in inflammatory states like septic shock. In addition, PKC activation enhances endothelial cell permeability resulting in edema. This response to inflammatory agents was also abrogated by exposure of the cells to the PKC inhibitor H7 (Lynch, J. J. et al. (1990) J. Clin. Invest. 85: 1991–1998). Abnormal leukocyte accumulation is implicated in a variety of inflammatory states such as: reperfusion injury, autoimmune diseases, and acute respiratory distress syndrome (ARDS). The damage is thought to result from the release of toxic oxygen radicals and proteases that potentiate tissue damage. The use of anti-adhesive protein antibodies or adhesive like proteins was shown to reduce tissue damage in select models of reperfusion injury (Vealder, N. B. et al. (1988), J. Clin. Inv. 81: 939–944; Simpson, P. J. et al. (1988) J. Clin. Inv. 81: 624–629; Horgan, M. J. et al. (1989) Am. J. Physiol. 259: L315–L319; International patent application of Vadas, M., and M. Berndt (1991) Application #WO 91/07993) and endotoxin induced damage (Rosen, H. and S. Gordon (1989) Br. J. Exp. Path 70: 385–394). When antibodies are used as a treatment they do not control the levels of expression of these proteins and the antibodies typically have short half-lives in circulation. An additional complication of antibodies is the potential for immunogenic reactions to large foreign proteins. Compared to antibodies, smaller molecules like antisense oligonucleotides can overcome these disadvantages and also provide selective control of expression of a single cellular protein.

The mRNA coding for VCAM-I has been cloned and the nucleic acid sequence is available for selective targeting with antisense oligonucleotides (Osborn, L. (1989) Cell 59: 1203–1211).

ANTISENSE BACKGROUND

The use of antisense oligonucleotides for therapeutic purposes was first proposed in 1978 by Stephenson, M. E. and P. C. Zamecnik ((1978) PNAS 75: 285–288). The concept behind antisense therapy relies on the ability of antisense oligonucleotides to be taken up by cells and form a stable heteroduplex with the target mRNA. The end result of antisense oligonucleotide hybridization is the down regulation of the targeted protein's synthesis. Down regulation of protein synthesis by antisense oligonucleotides has been postulated to result from two possible mechanisms: 1) "hybrid arrest", where direct blocking in pre-mRNA and/or mRNA of sequences important for processing or translation prevents full-length proteins from being synthesized; and 2) an RNase H mediated cleavage and subsequent degradation of the RNA portion of the RNA:DNA heteroduplex (Haeuptle, M. et al. (1986) Nuc. Acids Res. 14: 1427–1448; Minshull, J. and J. Hunt (1986) Nuc. Acids Res. 14: 6433–6451). Thus, the use of antisense oligonucleotides could down-regulate the expression of proteins or enzymes that are implicated in the etiology of a disease state. Down regulation of a protein is functionally equivalent to a decrease in its activity, the mechanism of action of most traditional pharmaceutical drugs.

The interaction of the antisense oligonucleotide with the target mRNA is highly specific as hybridization is determined by the sequence of bases complementary to the antisense oligonucleotide, or by the Watson/Crick base pairing of the two strands of nucleic acid. Thus, there are multiple points of contact between the antisense oligonucleotide and the mRNA target, which increases the specificity for hybridization to the correct sequence. This specificity derived from the Watson/Crick base pairing is not evident in traditional drugs that inhibit the activity of proteins or mimic their action. Potential side effects experienced with traditional drug therapies results through interactions at a few contact points between the drug and various proteins that possess similar binding sites or sites of interaction. Such adverse effects should be eliminated with antisense drugs. Experimental calculations using the number of base pairs in the human genome and the frequency of base utilization predict that there would be a single complement to a 14-mer antisense oligonucleotide in the entire human genome (Ts'o, P.O.P. et al. (1987) Biological Approaches to the Controlled Delivery of drugs, Vol 507, Ann. N.Y. Acad. Sci.). This level of specificity is not achievable with traditional drugs.

Evidence for down regulation of protein synthesis by antisense oligonucleotides has been well documented in vitro (for reviews see van der Krol, A. R. et al. (1988) BioTechniques 6: 958–976; Cohen, J. S. (1991) Antiviral. Res. 16: 121–133). In vivo studies using antisense oligonucleotides have demonstrated that injection of radiolabeled antisense oligonucleotides into the blood of mice results in distribution of full-length labeled oligonucleotide to the various tissues. Once in the tissue, oligonucleotides can elicit an antisense effect by binding to the correct mRNA and, thus, be suitable for a therapeutic approach to a disease state (Miller, P. S. and P.O.P Ts'o (1987) Anticancer Drug Design 2: 117–128). Recently, antisense oligonucleotides have been shown to elicit a reduction in myc gene expression using an in vivo mouse model for B-cell lymphoma myc expression (Wickstrom, E. et al. (1991) FASEB J. 5: A1442). Other in vivo data has shown that antisense oligonucleotides to 5' viral sequences of tick-borne encephalitis virus were capable of providing protection (30–50% survival in treated animals versus 100% lethality for control mice receiving no antisense oligonucleotide) in mice from viral induced death (Pogodina, V. V., et al. (1989) Dokl-Akad-Nauk-SSSR 308: 237–240). Further evidence for in vivo efficiency of antisense oligonucleotides in mice has shown that subcutaneous injection of a phosphorothioate oligonucleotide could inhibit the synthesis of interleukin-1 receptor protein (Burch, R. and L. C. Mahan (1991) J. Clin. Invest. 88: 1190–1196). The infiltration of neutrophils into the dermal injection site of IL-1 was used as a means of assessing the ability of injected antisense oligonucleotides to inhibit IL-1 receptor synthesis. It was shown that three, 3 nmole, subcutaneous injections of phosphorothioate anti-IL-1 receptor oligonucleotides (24 hr intervals) significantly reduced neutrophil infiltration. Control injections of saline or mismatch containing oligonucleotides did not inhibit neutrophil infiltration. Thus, antisense oligonucleotides targeted to the IL-1 mRNA were able to prevent IL-1 induced neutrophil infiltration in mice.

The stability, pharmacokinetics, and bio-distribution of antisense oligonucleotides in vivo have also been reported in mice. Using phosphorothioate antisense oligonucleotides, about 30% of either i.p. or i.v. injected oligonucleotide was retained in the animal with the remaining oligonucleotide being excreted in the urine (Agrawal, S. et al. PNAS 88: 7595–7599, 1991). The oligonucleotide retained within the animal was found within most tissues up to 48 hours. There were differences in the rates of degradation within the various tissues, with the plasma, stomach, heart and intestine showing the most intact oligonucleotide (15% degraded). In the kidney and liver degradation was 50% or greater after 48 hours. All of these experiments demonstrate that the antisense oligonucleotides are capable of reaching tissues in vivo and that the expression of gene products, proteins derived from mRNA translation, can be specifically down-regulated by antisense oligonucleotides in live animals.

A major issue to be addressed in the use of antisense oligonucleotides for in vivo treatment is the stability of the molecule to the action of nucleases. Use of unmodified oligonucleotides containing phosphodiester linkages has not proven valuable in antisense therapy since these oligonucleotides are susceptible to exo- and endonucleases present in serum and cells. Thus, modifications of the natural, or phosphodiester deoxyoligonucleotides (PO-ODN) have been developed that provide increased stability to degradation (for review Uhlmann, E. and A. Peyman (1990) Chemical Reviews 90: 543–584). One of these modifications is the replacement of one of the non-bridging oxygen atoms in the phosphodiester linkage with sulfur to produce a phosphorothioate deoxyoligonucleotide (PS-ODN). The introduction of sulfur atoms in the PS-ODNs do not disrupt hybridization significantly compared to unmodified PO-ODNs, retains the relative solubility of PO-ODNs in aqueous media and provides significantly enhanced resistance to serum and cellular nucleases (Stein, C. A. et al. (1988) Nuc. Acids Res. 16: 3209–3221: Campbell, J. M. (1990) J. Biochem. Biophys. Methods 20: 259–267). Other modifications include methylphosphonates, phosphorodithioate, sugar modifications, and heterocycle modifications (Goodchild, J. (1990) Bioconjugate Chem 1: 165–186). Of various modifications to oligonucleotides, the PS-ODNs are suitable for antisense approaches to in vivo therapy at the present time; however, as novel chemistries become available there may be many new chemical modifications of antisense oligonucleotides that have increased potential for therapeutic applications.

The bio-availability of antisense oligonucleotides to target cells is another important issue that arises in the use of oligonucleotides for therapy. Enhanced cellular uptake has been reported using a wide variety of techniques including LIPOFECTIN™ (Life Technologies, Gaithersburg, Md.) (Chiang, M-Y. et al. (1991) J. Biol. Chem. 266: 18162–18171), lipoproteins (de Schmidt, P. C. (1991) Nuc. Acids Res. 19: 4695–4700), and a wide variety of conjugates, including poly-L-lysine or cholesterol etc (for review see Goodchild, J. (1990) Bioconjugate Chem. 1: 165–186). The ability to increase the uptake of ODNs into cells will become more diverse as more data accumulates. Conjugation of cholesterol to the 5' end of an oligonucleotide resulted in a molecule that exhibited reduced serum clearance, due to reduced kidney excretion, compared to control ODNs (de Smidt, P. C. et al. (1991) Nuc. Acids Res. 19: 4695–4700). This conjugation of cholesterol to ODNs may result in increased delivery to liver cells via the LDL transport mechanism. Other possibilities for increasing cellular uptake include modulation of the 80 kDa surface protein putatively involved in transport of oligonucleotides into cells. The availability of more information on this protein may provide insight into certain modifications that increase the activity of the transporter (Loke, S. L., et al. (1989) Proc. Natl. Acad. Sci. USA 86: 3472–3478). The conjugation of ODNs to certain biological molecules that are taken up into cells by specific receptors may provide an in vivo advantage in antisense oligonucleotide delivery. For example, conjugation of folate to the oligonucleotide may provide a selective cellular uptake mechanism through the endocytosis mediated vitamin folate pathway (Leamon, C. P. and P. S. Low (1991) Proc. Nat. Acad. Sci. USA 88: 5572–5576). Conjugation of folate to antibodies has demonstrated that this approach with large macromolecules is feasible. Thus, conjugations, such as folate or other ligands recognized by receptors, or to agents that carry the ODNs into cells via endocytotic uptake pathways, may be an extremely useful approach to antisense therapy. There may also be other conjugations that would target oligonucleotides to specific cells or organs which would decrease the effective concentration of oligonucleotide needed in a specific therapy. However, present data suggests that antisense oligonucleotides with modifications like phosphorothioate or methyl phosphonate are capable of tissue distribution and cellular uptake. Thus, at the present time an oligonucleotide sufficiently stable to nuclease degradation should be distributed to the cells and undergo cellular uptake.

Recently, it has been reported that antisense PS-ODNs are capable of down-regulating the in vitro expression of one member of the immunoglobin superfamily adhesion proteins involved in cell-cell adhesion, ICAM-1 (Chiang, M-Y. et al. (1991) J. Biol. Chem. 266: 18162–18171). These data suggest that antisense oligonucleotides, particularly those stable to nucleases, like the phosphorothioate or 2'-O-methyl modified antisense oligonucleotides, are capable of inhibiting the expression of cell adhesion molecules. Thus, the use of antisense oligonucleotides in the down-regulation of ICAM-1 and other adhesion molecules should provide a basis for therapy and treatment of inflammatory disorders, particularly septic shock. Inhibition of the inflammatory response component of sepsis may provide the necessary protection to prevent the lethal consequences of septic shock brought about by the body's own immune system.

While there are several generalized locations within the linear nucleotide sequence of any mRNA that may provide an increased capacity for antisense oligonucleotide intervention with the flow of information from the gene to the protein product, there is, as of yet, no way to predict the optimum sequence for an active antisense oligonucleotide. Uhlman and Peyman (1990) discuss the potential mechanisms of action for antisense oligonucleotides as inhibition of splicing, polyadenylation, translocation, translation and ribosome movement along the mRNA but the actual selection of a particular sequence is only discussed in general terms. One can select antisense oligonucleotides that target nucleotide sequences anywhere in a particular mRNA (i.e. 5'-untranslated region, coding region, 3'-untranslated region, or combinations thereof) because one wants to inhibit the expression of that mRNAs protein. One would not want to select an antisense sequence that is complementary to one protein's mRNA when the objective is to inhibit the expression of another protein. However, the selection of an antisense sequence, anywhere (whether located in the 5'-untranslated region, coding region, 3'-untranslated region, or combinations, thereof) within the nucleotide sequence of the target protein's mRNA will not always produce active antisense compounds.

Recent literature shows a number of specific examples of very potent in vivo therapeutic efficacy for antisense oligonucleotides. The examples cited below show three different therapeutic targets that indicate the wide range of therapeutic activity for antisense oligonucleotides.

The first study (Simons, M. et al., 1992, Nature 359: 67–70) shows that an antisense phosphorothioate directed against c-myb can be delivered in vivo to rat carotid arteries stripped of their intima. The oligonucleotides were formulated in a pluronic gel containing 200 micrograms of drug and applied to the outer layer of the arteries. The drug had to reach the smooth muscle cells surrounding the intimal layer, in order to have a therapeutic effect. Indeed, the antisense oligonucleotide effectively prevented restenosis or regrowth of smooth muscle cells around the stripped regions. This effect indicates strongly that antisense can be therapeutically effective in living rats in a stringent model.

A second study shows that a human leukemia can be treated successively in a scid mouse model with antisense oligonucleotides against c-myb (Ratajczak, M. Z. et al., 1992, Proc. Natl. Acad. Sci. USA 89: 11823–11827). This work established human leukemia-scid mouse chimeras with K562 cells and treated diseased animals with phosphorotioate-modified antisense oligonucleotides against c-myb. The results showed that control oligonucleotides had no effect on survival, whereas animals treated with antisense constructs survived at least 3.5 times longer than the various control animals. Antisense treated animals had significantly less disease at sites where leukemia is often refractory to treatment, the brain and the ovary. The drug was delivered to the animals by Alzet minipumps that released 1.0 microliter per hour into a paraspinal pocket at a 100 microgram per day so that each animal received 5 mg/kg or 1.0 micromolar dose. Thus, based on the results of this animal model, it seems quite reasonable that antisense may have efficacy in this and other cancer models.

A third study shows that antisense oligonucleotides to the NMDA-R1 receptor channel can protect cortical neurons of rats from excitotoxicity and reduce focal ischemic infarctions (Wahlestedt, C. et al., 1993, Nature 363: 260–263). In this rat model of stroke, antisense therapy was more effective than MK-801, the most effective small molecule therapy for stroke. The antisense drug was delivered intraventricularly in a dose of 15 nmol in 5 µl $H_2O$. The appropriate controls had no effects.

In summary, these data show that antisense therapy applied to stringent animal models of human disease can cause profound therapeutic benefits in the models. One can thus say that, while there is more in vitro antisense data, the efficacy seen in these animal models is sufficient to predict that there may be profound therapeutic benefit in humans from antisense drugs discovered in vitro. Of course this is precisely the situation for standard small molecule drugs discovered in vitro.

Investigations into the toxicity of antisense oligonucleotides has not revealed significant damage or lethality to cells. In vitro studies into the toxicity of antisense oligonucleotides has been limited primarily to modified oligomers where the phosphodiester linkages between the sugar moieties has been replaced with either phosphorothioates or methylphosphonates. Generally, phosphorothioates are nontoxic in a variety of cell lines (for example, Reed, J. C. et al. (1990) Cancer Res. 50: 6565–6570).

SUMMARY OF THE INVENTION

Accordingly, an object of the invention is a therapy to lessen morbidity and mortality caused by septic shock and the ensuing complications and associated symptoms.

An additional object of this invention is a method of treating the symptoms of septic shock.

Yet another object of this invention are agents to prevent vascular and tissue defects associated with manifestations of septic shock.

Another object of this invention is a formulation of an inhibitor of the inflammatory response that is a major cause of the complications resulting in septic shock.

An additional object of this invention is a method for inhibiting the adhesion of leukocytes to the endothelium of the vasculature, where the adhesion of leukocytes to the endothelium is the initial event in the development of the inflammatory response.

The foregoing objects of the present invention are accomplished by providing an improved therapeutic treatment for the collective diseases of 'sepsis' that result from inflammatory response mediated changes in the vasculature by using nucleic acids, either as oligonucleotides or polynucleotides, as antisense inhibitors of protein translation, specifically VCAM-I.

These and additional objects of the invention are accomplished by treating the subject susceptible to septic shock with antisense oligonucleotide, preferably with a sequence which inhibits synthesis of the protein VCAM-I. Preferred are those oligonucleotides which substantially form a stable hybrid with at least a portion of the gene or mRNA coding for VCAM-I. Preferred is an oligonucleotide that comprises a sequence that forms a stable hybrid with at least a portion of the 5' UTR (UnTranslated Region), translation initiation codon, coding region, or 3' UTR of the pre- or mature-mRNA for VCAM-I. Other preferred sites include the remaining regions of the exons of the gene and the intron regions to inhibit pre-mRNA processing. The inhibitors of this invention are administered, preferably by intravenous infusion in a suitable pharmaceutical carrier, in a range of 0.01 to 500 mg/Kg body weight preferably in the range of 0.05 to 250 mg/Kg body weight and most preferably in the range of 0.15 to 50 mg/Kg body weight.

In preferred embodiments, these antisense oligonucleotides comprise a nucleotide sequence that forms heteroduplexes within the 5' untranslated region of the mRNA, the translational initiation codon, the sequence immediately downstream from the translation initiation codon, unique portions of the 3' untranslated regions, or combinations thereof. These oligonucleotides may comprise from a 10- to a 30-mer.

The oligonucleotide can be used to inhibit the expression of the human VCAM-I. Thus, the invention encompasses the use of at least one oligonucleotide, alone or in combination in the therapeutic treatment of patients suffering from septic shock or the resultant complications from sepsis.

In a preferred embodiment of the invention, a therapeutically effective concentration of oligonucleotide can be administered to a patient so as to substantially block the translation of the human VCAM-I mRNA, thereby substantially reducing the complications of sepsis.

The present invention also provides a pharmaceutical composition comprising one or more oligonucleotides of the invention in combination with a suitable pharmaceutical carrier according to conventional pharmaceutical techniques.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

In accordance with the detailed description, the following definitions apply:

Antisense oligonucleotides—any natural or modified oligonucleotide or chemical entity that binds specifically to a pre-mRNA or mature mRNA which results in interference or inhibition with translation of the mature mRNA or prevents the synthesis of the polypeptide encoded by the mature mRNA.

Septic shock—septic shock is used in this invention to convey any of the various states of the collective diseases known as sepsis, sepsis syndrome, septic shock, incipient septic shock, bacteremia, refractory septic shock, or any of the diseases associated with sepsis such as ARDS (adult respiratory distress syndrome), multiple organ failure, cardiac dysfunction, etc.

VCAM-I—VCAM-I in this invention describes the Vascular Cell Adhesion Molecule -I involved in adherence of leukocytes (monocytes and neutrophils especially).

mRNA—mRNA refers to mature, processed mRNA or unprocessed, nuclear pre-mRNA (ribonucleic acid) to the ribonucleic acid transcribed from the gene(s) encoding for the synthesis of VCAM-I. These sequences of ribonucleic acid are used to select the antisense oligonucleotide sequences which are complementary to discrete portions of the mRNA or pre-mRNA.

As used herein, unless otherwise indicated, the term "oligonucleotide" includes both oligomers of ribonucleotides i.e. oligoribonucleotides, and oligomers of deoxyribonucleotides i.e. oligodeoxyribonucleotides, or oligodeoxynucleotides.

Unless otherwise indicated, the term "oligonucleotide" also includes oligomers which may be large enough to be termed "polynucleotides".

The terms "oligonucleotide" and "oligodeoxynucleotide" include oligomers and polymers of biologically significant nucleotides, adenine, deoxyadenine, guanine, deoxyguanine, thymine, uracil, cytosine and deoxycytosine, as well as oligomers and polymers which contain other novel nucleotides and are hybridizable to the target mRNA transcript. These terms also include oligomers and polymers having one or more purine or pyrimidine moieties, sugar moieties, or internucleotide linkage(s) which has or have been chemically modified. Such modifications may be substantial and may encompass nonnucleotide chemistries including non-sugar, non-phosphate backbone, and chemical alterations to the bases to maintain the specific hybridization to the mRNA by base-pairing mechanisms, similar to or different from Watson-Crick base pairing. These terms further include those oligomers or polymers that are composed of nucleoside containing bases joined to the sugar moieties in the alpha configuration.

The term "downstream" is used herein to indicate the 5' to 3' direction in a nucleotide sequence. Similarly, the term "upstream" indicates the 3' to 5' direction.

The term "complementary" is used herein to indicate that the oligonucleotide is capable of hybridizing to and forming a duplex with its target sequence in the mRNA transcript.

The term "stable duplex" or a "stable hybrid" is used herein to indicate that 50% or greater of the oligonucleotide is bound in said duplex with its target sequence in the mRNA transcript at a temperature of 40° C. in 10 mM sodium phosphate, 1 mM ethylenediamine tetraacetic acid and 128 mM sodium chloride, pH 7.

The term "mRNA" is used herein to indicate either the mature or processed mRNA, or the unprocessed nuclear pre-mRNA.

According to a preferred embodiment of the present invention, antisense oligonucleotides are synthesized using standard published techniques for the synthesis of phosphorothioate, PS, oligonucleotides. Synthesis of antisense oligonucleotides is performed using a solid support and a commercially available DNA synthesizer. Antisense oligonucleotides are synthesized using standard phosphoramidate chemistry. For phosphodiester linkages the oxidation is mediated via iodine, while for the synthesis of phosphorthioates, the oxidation is mediated with a 0.2M solution of 3H-1,2-benzodithiole-3-one, 1,-dioxide in acetonitrile (Iyer, R. P., et al. (1990) J. Amer. Chem. Soc. 112: 1253–1254) for the step-wise thioation of the phosphate linkages. The thioation step is increased to 68 sec and is followed by a capping step. Following synthesis and cleavage from the control pore glass support, the trityl-on oligonucleotide is purified using HPLC. HPLC methodologies consist of chromatography using an PRP-1 column and gradient of acetonitrile in 50 mM triethylammonium acetate, pH 7.0 (4–32% in 30 min, flow rate of 1.5 ml/min). Appropriate fractions are pooled, evaporated, treated with 5% acetic acid for 15 min at ambient temperature. The oligonucleotide solution is extracted with an equal volume of ethyl acetate, neutralized with ammonium hydroxide, frozen and lyophilized. Solution based chemistries are also useful for synthesis of antisense oligonucleotides and are useful for scaled-up synthesis Of oligonucleotides.

DETAILED DESCRIPTION OF THE INVENTION

The present invention is concerned with oligonucleotides having therapeutic value, therapeutic compositions containing these oligonucleotides and methods for use thereof. The present invention is the result of research on septic shock and the role of inflammation in the resultant morbidity or mortality resulting from septic shock. Accumulated information has led to the conclusion that disruption of the inflammatory response would be a method of choice in the treatment of septic shock and the resulting complications.

It has previously been demonstrated in a number of systems by various investigators that oligonucleotides complementary in sequence to a portion of a particular mRNA are capable of hybridizing to the mRNA and inhibiting the translation of the transcript.

In accordance with the present invention, an oligonucleotide having a base sequence capable of hybridizing to the mRNA transcript of the human VCAM-I adhesion receptor is provided. Hybridization of the oligonucleotide to the VCAM-I mRNA substantially blocks the translation of the mRNA transcript. Because VCAM-I is essential for the initial attachment or adhesion of leukocytes arising from stimulations that induce septic shock, down-regulation of VCAM-I expression would provide a benefit to the patient in the form of a reduced inflammatory response.

The oligonucleotides of the present invention are constructed and purified by methods known in the art. The specific oligonucleotide sequence is complementary to a portion of VCAM-I mRNA or gene. In particular, the oligonucleotide sequence is complementary to a portion of VCAM-I transcript, such as the portion of the transcript including the translation initiation codon, and sequences 5' and/or 3' to the translation initiation site, of the 5' cap region of the mRNA and sequences 3' to the cap site. Another oligonucleotide sequence is also made complementary to a sequence contained in the 3' untranslated region of the VCAM-I gene that is substantially unique to the VCAM-I gene. Moreover, antisense oligonucleotides that are capable of cross-linking DNA or intercalating DNA can be made complementary to any portion of the VCAM-I gene. Furthermore, the invention contemplates that any oligonucleotide or combination of oligonucleotides capable of specifically and substantially inhibiting the expression of VCAM-I can be used.

The oligonucleotides of this invention comprise predetermined sequences of DNA ranging in size from about 10 bases up to about 30 bases, which is sufficient to define a unique sequence in the human VCAM-I target mRNA transcript. Alternatively, two or more oligonucleotides of 7–15 bases may be joined together by non-nucleotide linkages. For such oligonucleotides less than 14 bases may be used, however the degree of sequence uniqueness decreases rapidly with decreasing length and thereby greatly reduce the specificity of the oligonucleotide for the VCAM-I mRNA transcript. On the other hand, oligonucleotide sequences greater than about 30 bases may be subject to decreased cellular uptake and have an increased likelihood of containing short stretches of nucleotide sequence that is capable of forming quasi-stable hybrids with non-target mRNA sequences, other than the VCAM-I mRNA transcript. It is preferable that the oligonucleotides comprise about 15 to 25 bases. In the most preferred embodiment of this invention, a 21-mer oligonucleotide is used, to be selected from the group of at least GCC TGG GAG GGT ATT CAG CTC (Seq I.D. No. 1); AAC CCF TAT TTG TGT CCC ACC (Seq I.D. No. 2); CCC AGG CAT TTT AAG TTG CTG (Seq I.D. No. 3); CAC GAG GCC ACC ACT CAT CTC (Seq I.D. No. 4); CTT TGA CTT CTT GCT CAC AGC (Seq I.D. No. 5); AAC TCC TCC AGT TCT CTC ATC (Seq I.D. No. 6); TTT AAG CAA TCT TGC TAT GGC (Seq I.D. No. 7); TCC TGA AGC GAG TGA GGC CCG (Seq I.D. No. 8); ACC TGT GTG TGC CTG GGA GGG (Seq. I.D. No. 9); CGT GAT GAG AAA GTG GTT (Seq I.D. No. 10); CGA CCA TCT TCC CAG GCA TTT (Seq I.D. No. 11); CCA CCA CTC ATC TCG (Seq I.D. No. 12); CCC ATT CAC GAG GCC ACC (Seq I.D. No. 13); CGA GGC CAC CAC TC (Seq I.D. No. 14); CCT CCA GTT CTC TC (Seq I.D. No. 15); CTC TCA TCT TGA TGG C (Seq I.D. No. 16); GCC AGT GAG GCC CG (Seq I.D. No. 17); CCT GGG AGG GTA TTC (Seq I.D. No. 18); CCC TTA TTT GTG TCC C (Seq I.D. No. 19); GGT TCC AAA ACC CTT (Seq I.D. No. 20); TTT GTG TCC CAC CTG (Seq I.D. No. 21.); and CAT CTT CCC AGG CAT (Seq I.D. No. 22) wherein the sequences as listed are in the 5' to 3' direction.

The oligonucleotide sequence may be prepared by solid phase or solution phase synthesis in an automated nucleic acid sythesizer or via solution phase techniques. Also, in a less preferred method, the oligonucleotide may be prepared through the use of reverse transcriptase, PCR synthesis, or via other genetic engineering techniques. The method of preference for this invention is synthesis of the oligonucleotide using automated DNA synthesis on a solid phase support. Any means of synthesis of the oligonucleotides is within the scope of this invention.

Modifications to the oligonucleotides may be used to increase several desirable properties, including solubility, enhanced uptake, or enhanced stability to degradation, for example. Thus, modifications to the phosphate backbone, termini, sugar moiety, or the individual nucleic acid bases are within the scope of this invention. A preferred modification to the oligonucleotides is the alteration of the phosphodiester linkage between the sugar moieties. A more preferred embodiment of this invention is the use of phosphorothioate linkages between the sugar moieties. The combination of various modifications, for example, phosphate backbone modifications in combination with any number of terminal conjugates, is within the scope of this invention. The terminal modifications may include cross-linking agents, intercalators, photochemically activated moieties, alkylating agents and redox active nucleic acid cleavage groups. Also included are modifications that are nonnucleotide based in chemistry but that still form stable heteroduplexes with at least a portion of the VCAM-I mRNA. For example, non-nucleotide i.e. $(CH_2)_n$ linkers between oligonucleotides are included.

The composition of the present invention comprises at least one oligonucleotide having a nucleotide sequence at least substantially complementary to at least a portion of the human VCAM-I mRNA transcript in a suitable pharmaceutical carrier. The amount of oligonucleotide in the composition can range from about 0.01% to 99% by weight of the composition. The oligonucleotide can be mixed with a variety of carrier compounds depending upon the form of the preparation desired for administration, e.g. delivery by i.v modalities. The more preferred means of delivery is via an i.v. solution prepared with any of the usual pharmaceutical components.

Figure 1:
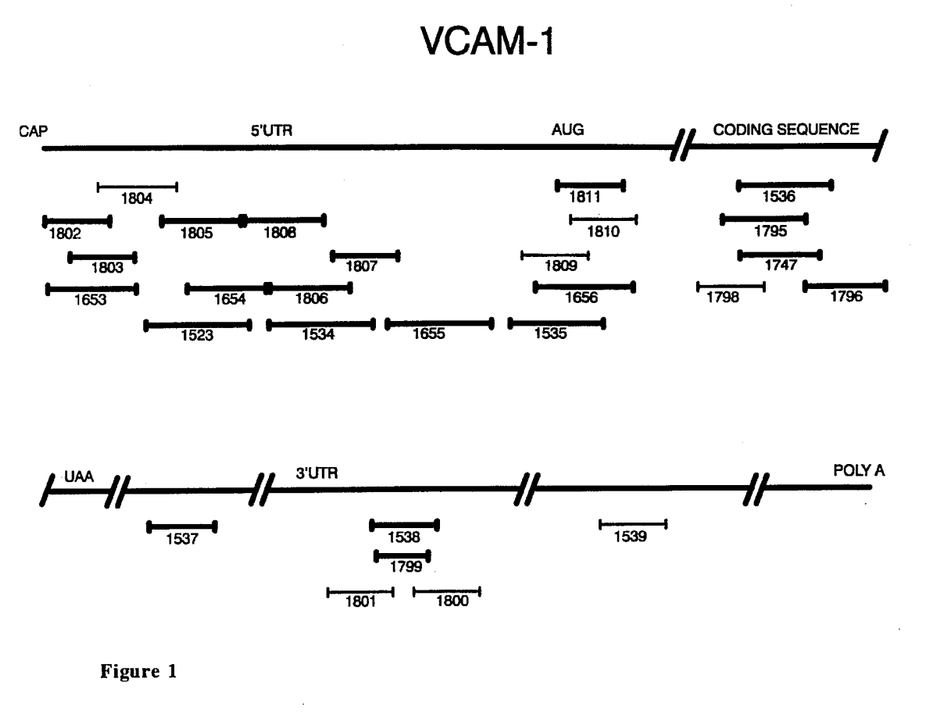
FIG. 1 is a map of VCAM-1 showing the oligonucleotides of the invention.

The selection of antisense oligonucleotides that exhibit activity against a particular mRNA requires the determination of active antisense oligonucleotides experimentally. For example, data obtained from evaluating the capacity for a series of antisense oligonucleotides targeting the mRNA for Vascular Cell Adhesion Molecule-1 (VCAM-1) to inhibit expression of the protein product revealed that there were no generalized rules for the selection of the antisense oligonucleotides that exhibited optimum or even sub-optimum activity (Table 1). The mRNA for VCAM-1 is 2,811 nucleotides in length. The length of the 5'-untranslated region is 106 nucleotides, the coding region 1,941 nucleotides long, and the 3'-untranslated region is 764 nucleotides in length. Assuming that one wishes to design antisense oligonucleotides 21 nucleotides in length there are 2,790 potential 21-mers that could be synthesized. However, many of these 2,790 oligonucleotides will not exhibit sufficient activity to inhibit translation of the VCAM-1 mRNA. Experimental determination of the capacity for 28 different antisense oligonucleotides to inhibit VCAM-1 protein synthesis revealed that approximately 50% of the synthesized oligonucleotides did not significantly inhibit VCAM-1 protein synthesis (greater than 50% inhibition at 0.1 μM) as depicted in FIG. 1 where the long bar denotes the mRNA sequence of human ICAM-1. The 5'cap, untranslated regions (UTR), start codon (AUG), coding sequence, termination codon (UAA) and polyadenylated tail are enumerated above the bar. Gray areas denote intron regions. The shorter bars denote oligodeoxynucleotides (ODN) that have been evaluated for their ability to suppress expression of ICAM-1 in human umbilical vein endothelial cells. The code number for each ODN is printed just below the bars. All ODNs were evaluated at 0.1 μM. Bold bars represent ODNs that inhibit ICAM-1 expression greater than 50%

In these experiments, antisense oligonucleotides were added to human umbilical vein endothelial cells (HUVEC) in the presence of 10 μg/ml Lipofectin (Life Technologies, Gaithersburg, Md.) in serum free media for 4 hours. Media containing oligonucleotide was removed and media containing 10% fetal calf serum was added.

TABLE 1

| VCAM-1 ANTISENSE OLIGONUCLEOTIDES | | | | | |
|---|---|---|---|---|---|
| Oligo-nucleotide[1] | Location[2] | Length (Nucleotides) | % GC[3] | Tm[4] | % Inhibition[5] |
| GM1534 | 48–68 | 21 | 47.6 | 64.7 | 90 |
| GM1806 | 51–66 | 16 | 50.0 | 52.3 | 63 |
| GM1807 | 62–76 | 15 | 46.7 | 50.5 | 58 |
| GM1808 | 46–60 | 15 | 53.3 | 49.5 | 89 |
| GM1799 | 2258–2272 | 14 | 57.1 | 38.5 | 68 |
| GM1800 | 2269–2286 | 18 | 50.0 | 55.4 | 18 |
| GM1801 | 2248–2263 | 16 | 50.0 | 48.0 | 45 |
| GM1535 | 95–115 | 21 | 47.6 | 66.8 | 67 |
| GM1656 | 105–125 | 21 | 52.4 | 70.3 | 81 |
| GM1809 | 101–115 | 15 | 46.7 | 49.8 | 22 |
| GM1810 | 113–126 | 14 | 57.1 | 46.9 | 49 |
| GM1811 | 107–121 | 15 | 57.1 | 51.6 | 55 |

[1]Oligonucleoties - modified using phosphorothioate chemistry.
[2]Location - represents the number of nucleotides in the mRNA that are complementary to the antisense sequence.
[3]% GC - represents the percentage of guanine and cytosine nucleo-bases comprising the total nucleotide composition of the oligonucleotide.
[4]Tm - represents the predicted Tm (represents the temperature, °C., where the strands are half dissociated or denatured. These values are predicted using the nearest neighbor approach (Breslauer et al., 1986, Proc. Natl. Acad. Sci. 83: 3746–3750 and Freier, et al., 1986, Proc. Natl. Acad. Sci. 83: 9373–9377).
[5]% Inhibition - represents the percent decrease in IL-1β (10 U/ml)-induced VCAM-1 protein expression. Cells (human umbilical vein endothelial) were treated with 100 nM oligonucleotide prior to VCAM-1 induction. VCAM-1 expression was determined 24 hours post-induction.

Approximately 16 hours later, VCAM-1 protein synthesis was induced by the addition of either interleukin-1β (10 U/ml) or lipopolysaccharide, LPS (0.5 μg/ml). These compounds caused marked induction of VCAM-1 protein expression as determined by a radio-immuno assay. Evaluation of the data demonstrated that there were no rules or obvious sequence locations that consistently predict active antisense oligonucleotides. For example, in the 3'-untranslated region antisense oligonucleotide GM1800 did not significantly inhibit VCAM-1 expression (18%). This oligonucleotide spans VCAM-1 mRNA nucleotides 2273–2286. However, antisense oligonucleotides 1799 and 1801, which span VCAM-1 nucleotides 2258–2272 and 2248–2263, respectively, exhibited the capacity to significantly inhibit VCAM-1 expression. These sequences are not located near any particular mRNA consensus sequences, such as the potential cleavage or proposed polyadenylation signals (i.e. AAUAAA Wickens and Stephenson, 1984, Science 226: 1045–1051) or destabilizing sequences (i.e. the ARE sequence AUUUA, Shaw and Kamen, 1986, Cell 46: 659–667). The reason for the observed differences in antisense activity for these oligonucleotides, i.e., relative lack of activity for GM1800, is not obvious. Examination of the predicted Tm (based upon the nearest neighbor approach) for these three antisense oligonucleotides reveals that the more active antisense sequences, GM1799 and GM1801, have predicted Tms of 38.5° and 48.0° C. while the Tm for the more inactive sequence, GM1800 is 55.4° C. Thus, antisense activity or lack of activity can not be determined based upon the Tm (or G/C content) of potential antisense oligonucleotides.

In the 5'-untranslated region there are similar ranges of activities for antisense oligonucleotides that target the same or adjacent nucleotide sequences in the VCAM-1 mRNA. For example, the 15-mer antisense oligonucleotide GM1807, spanning nucleotides 62–76, exhibited moderate antisense activity (58%). However, by moving the bases toward the 5' end of the mRNA to produce a 15-mer complementary to nucleotides 46–60, there is an increase in activity (GM1808 exhibited 89% inhibition). By expanding the 15-mer to a 21-mer by extending the 5' and 3' ends of GM1808 to produce an oligonucleotide complementary to nucleotides 48–68 did not significantly increase the activity of GM1808 (GM1534 exhibited 90% inhibition)) As with GM1799, GM1800, and GM1801, there are no obvious reasons for this difference in activity. The oligonucleotide GM1808 (Tm=49.5° C.), complementary to nucleotides 46–60 demonstrated significant antisense activity while GM1807 (Tm=50.5° C.), complementary to 62–76 was not as active. Taken together, the data obtained in the 5'-untranslated region with these oligonucleotides does not suggest any obvious rationale for their activities. Activity is not based on length (GM1808, a 15-mer, is more active than GM1807, also a 15-mer,) or duplex stability. The predicted Tm for GM1799 (exhibiting 68% inhibition of VCAM-1 expression) is approximately 17° C. less than the Tm for GM1800 (exhibiting 18% inhibition). That hybridization to a particular sequence of mRNA nucleotides is not sufficient to predict activity is demonstrated by the following example taken from the 5'-untranslated region. The antisense oligonucleotides GM1656 (complementary to nucleotides 105–125) exhibited antisense activity (81% inhibition). However, the three oligonucleotides GM1809, GM1810, and GM1811 all failed to produce similar levels of inhibition. These three oligonucleotides are complementary to nucleotide sequences 101–115, 113–126, and 107–121, respectively. Thus, these three oligonucleotides, GM1809, GM1810, and GM1811, span the nucleotide sequence from 101–126, which encompasses the nucleotides complementary to GM1656 (nucleotides 105–121). That a 15-mer can exhibit antisense activity has already been demonstrated above (GM1808). However, these oligonucleotides do not exhibit significant inhibition of VCAM-1 expression.

Figure 2:
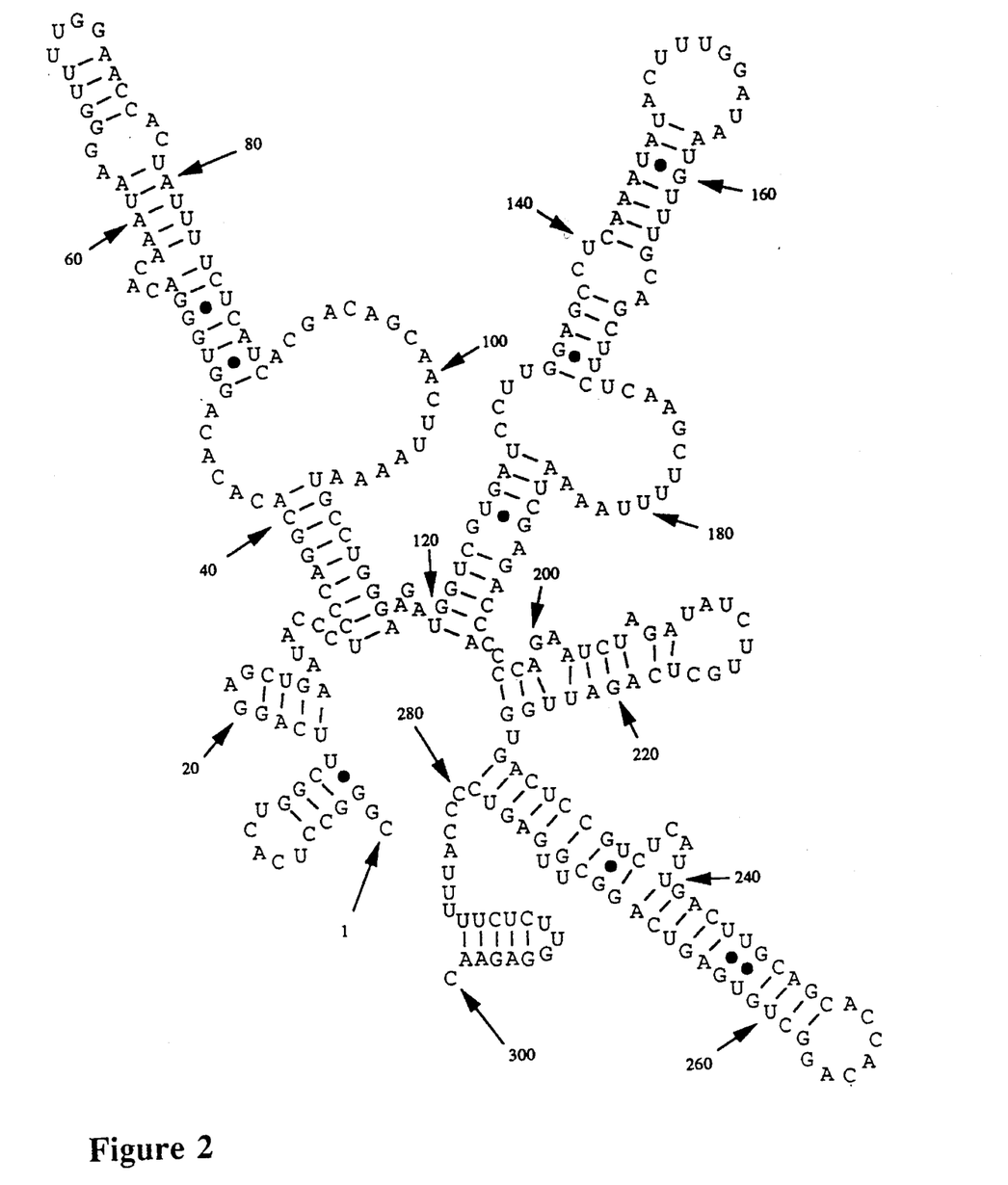
FIG. 2 is the predicted secondary structure for 5'-untranslated end (nucleotides 1–300) of human VCAM-1 mRNA (free energy for formation=–64.2 kcal/mol)

Based upon the above discussions of antisense activity for oligonucleotides that are similar in length and complementary to the same nucleotides, there are no rational explanations or rules that would predict active sequences. There have been suggestions that mRNA secondary structures might be important factors that would make the selection of an active antisense oligonucleotide obvious. FIG. 2 shows the secondary structure that would be present in nucleotides 1–300 for the 5' end of VCAM-1 mRNA. The predicted free energy for this structure is –63.7 kcal/mole. There does not appear to be any obvious feature of the mRNA secondary structure that would suggest that oligonucleotides complementary to that sequence would exhibit antisense activity. For example, GM1808 and GM1806 (complementary to nucleotides 46–60 and 51–66, respectively) were designed to bind to nucleotides within the stem structure that spans nucleotides 48–90. However, the ability to inhibit VCAM-1 expression was 89 and 63 percent, respectively. While both of these oligonucleotides were designed to bind with relatively similar thermodynamic stability (predicted Tms of 49.5° and 52.3° C., respectively) and to regions contained within one side of the predicted stem structure, they exhibited differences in their ability to inhibit expression. Another example of the inability of mRNA secondary structure predictions to be used in selecting active antisense oligonucleotides is demonstrated by oligonucleotides GM1799, GM1800, and GM1801. While these three antisense oligonucleotides target within similar regions of VCAM-1 mRNA sequence, there are no obvious secondary structures that would have predicted that GM1799 (nucleotides 2258–2272) would exhibit more activity than GM1800 or GM1801 (nucleotides 2269–2286 or 2248–2263, respectively).

Based upon the above discussion of the data obtained in the analysis of antisense oligonucleotides targeting the mRNA for human VCAM-1, there are no obvious regions of a target mRNA that can be predicted to be effective targets for antisense oligonucleotide-induced down regulation of protein synthesis. The selection of any specific oligonucleotide sequence that exhibits antisense activity requires rigorous experimental evaluation of a number of antisense sequences. The experimental determination for VCAM-1 antisense sequences suggest that there are only generalized regions of the mRNA for selecting an active antisense oligonucleotides that can significantly inhibit the expression of a particular protein. This lack of predictive activity, lead us to evaluate many different regions of nucleotide sequence in the human CD18 mRNA. After analysis of the data only those oligonucleotides that exhibit significant inhibition of CD 18 protein expression were selected for further analysis.

The following examples illustrate the principles and practices of the invention and are not intended to limit its scope in any way.

EXAMPLE 1.

This example describes the preparation and use of a series of oligonucleotides whose base sequences are complementary to sequences contained in the human LFA-1 mRNA transcript. The oligonucleotides are synthesized on an automated DNA synthesizer using standard techniques practiced in the art.

Phosphorothioate oligonucleotides are synthesized using standard procedures (Iyer, R. P. et al. (1990) J. Amer. Chem. Soc. 112: 1253–1254). A sequence of one of these phosphorothioate oligonucleotides, complementary to the 5' untranslated region and translation initiation codon, is 5'- CCC AGG CAT TTT AAG TTG CTG-3', where the translation initiation codon is underlined and in bold face type. This oligonucleotide is known by the name GM1535. GM1535 is prepared for delivery to the vasculature using an i.v. solution containing the oligonucleotide. The antisense oligonucleotide is presented to the lining of the vasculature (the endothelium cells expressing VCAM-I) taken up by the cells and forms a stable heteroduplex with the mRNA transcript that codes for VCAM-I. This hybridization of the oligonucleotide to the mRNA results in a down-regulation of VCAM-I synthesis. Due to the down-regulation of VCAM-I synthesis, there is a reduction in the cell membrane presentation of VCAM-I. With a down-regulation of VCAM-I there is a reduction in the adhesion of leukocytes to the endothelium, and thus, a reduction in the inflammatory response.

The frequency and duration of i.v. oligonucleotide therapy, concentration of oligonucleotide in the i.v. fluid will vary from patient to patient and can be determined by the prescribing physician. While the inflammatory response is being abated by the antisense oligonucleotide therapy, the use of standard therapies are used to control the bacterial or other infection that resulted in the manifestation of the septic shock.

EXAMPLE 2.

The inhibitors of this invention are administered, preferably by intravenous infusion in a suitable pharmaceutical carrier, in a range of 0.01 to 500 mg/Kg body weight preferably in the range of 0.05 to 250 mg/Kg body weight and most preferably in the range of 0.15 to 50 mg/kg body weight. The oligonucleotide analogues do not rapidly enter cells. To improve cell entry, the oligonucleotide can be delivered together with a membrane permeablizing agent like polyoxyethylene sorbitan mono-oleate (Tween 80) or polyethylene glycol 300 molecular weight (PEG 300). Alternatively, the oligonucleotide solutions can be prepared by including it as an encapsulated material in a liposome suspension by any of several techniques. Alternatively, oligonucleotides are conjugated to compounds which expand the lifetime of the material in the circulating blood and enhance endothelial cell uptake. An example of a suitable conjugation moiety would be the vitamin folate. Obviously, many modifications and variations of the present invention are possible in light of the above teachings. It is therefore to be understood that, within the scope of the appended claims, the invention may be practiced otherwise than as specifically described.

What is claimed is:

1. An oligonucleotide having a nucleotide sequence complementary to a sequence contained in the pre-mRNA or mature mRNA transcript of human VCAM-1, said oligonucleotide selected from the group consisting of:

GCC TGG GAG GGT ATT CAG CTC (Seq I.D. No. 1):
AAC CCT TAT TTG TGT CCC ACC (Seq I.D. No. 2):
CCC AGG CAT TTT AAG TTG CTG (Seq I.D. No. 3):
CAC GAG GCC ACC ACT CAT CTC (Seq I.D. No. 4):
CTT TGA CTT CTT GCT CAC AGC (Seq I.D. No. 5):
AAC TCC TCC AGT TCT CTC ATC (Seq I.D. No. 6):
ACC TGT GTG TGC CTG GGA GGG (Seq I.D. No. 9):
CGT GAT GAG AAA ATA GTG GTT (Seq I.D. No. 10):
CGA CCA TCT TCC CAG GCA TTT (Seq I.D. No. 11):

CCA CCA CTC ATC TCG (Seq I.D. No. 12):
CCC ATT CAC GAG GCC ACC (Seq I.D. No. 13):
CGA GGC CAC CAC TC (Seq I.D. No. 14):
CCT CCA GTT CTC TC (Seq I.D. No. 15):
GCC AGT GAG GCC CG (Seq I.D. No. 17):
CCT GGG AGG GTA TTC (Seq I.D. No. 18):
CCC TTA TTT GTG TCC C (Seq I.D. No. 19):
GGT TCC AAA ACC CTT (Seq I.D. No. 20):
TTT GTG TCC CAC CTG (Seq I.D. No. 21), and
CAT CTT CCC AGG CAT (Seq I.D. No. 22).

2. The oligonucleotide according to claim 1 wherein the oligonucleotide consists of the sequence 5' CCC AGG CAT TTT AAG TTG CTG 3' (Seq I.D. No. 3).

3. The oligonucleotide of claim 1 wherein the oligonucleotide is a phosphorothioate oligonucleotide.

* * * * *